United States Patent [19]

Freiberg et al.

[11] Patent Number: 4,686,207

[45] Date of Patent: Aug. 11, 1987

[54] ERYTHROMYCIN A 11,12-CARBONATES AND METHOD OF USE

[75] Inventors: Leslie A. Freiberg; David J. Bacino, both of Waukegan, Ill.

[73] Assignee: Abbott Laboratories, North Chicago, Ill.

[21] Appl. No.: 797,343

[22] Filed: Nov. 12, 1985

[51] Int. Cl.⁴ .................. A61K 31/71; C07H 17/08
[52] U.S. Cl. ........................... 514/29; 536/7.2
[58] Field of Search .................... 514/29; 536/7.2

[56] References Cited

U.S. PATENT DOCUMENTS 3,842,068  10/1974  Tadanier et al. .............. 536/7.2
4,476,298  10/1984  Morimoto et al. ............. 536/7.2

Primary Examiner—Johnnie R. Brown
Attorney, Agent, or Firm—Martin L. Katz; Michael J. Roth

[57] ABSTRACT

Disclosed herein are erythromycin derivatives of the formula

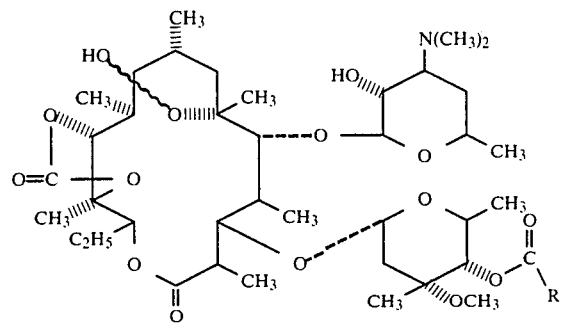

wherein $R_1$ is lower alkyl, aryl, alkene, aryl halide, alkylamino, hydroxyalkyl and furanyl, and pharmaceutically acceptable salts thereof. These compounds have improved oral absorption, reduced effects on gastrointestinal motility, increased acid stability and longer serum half-lives.

3 Claims, 1 Drawing Figure

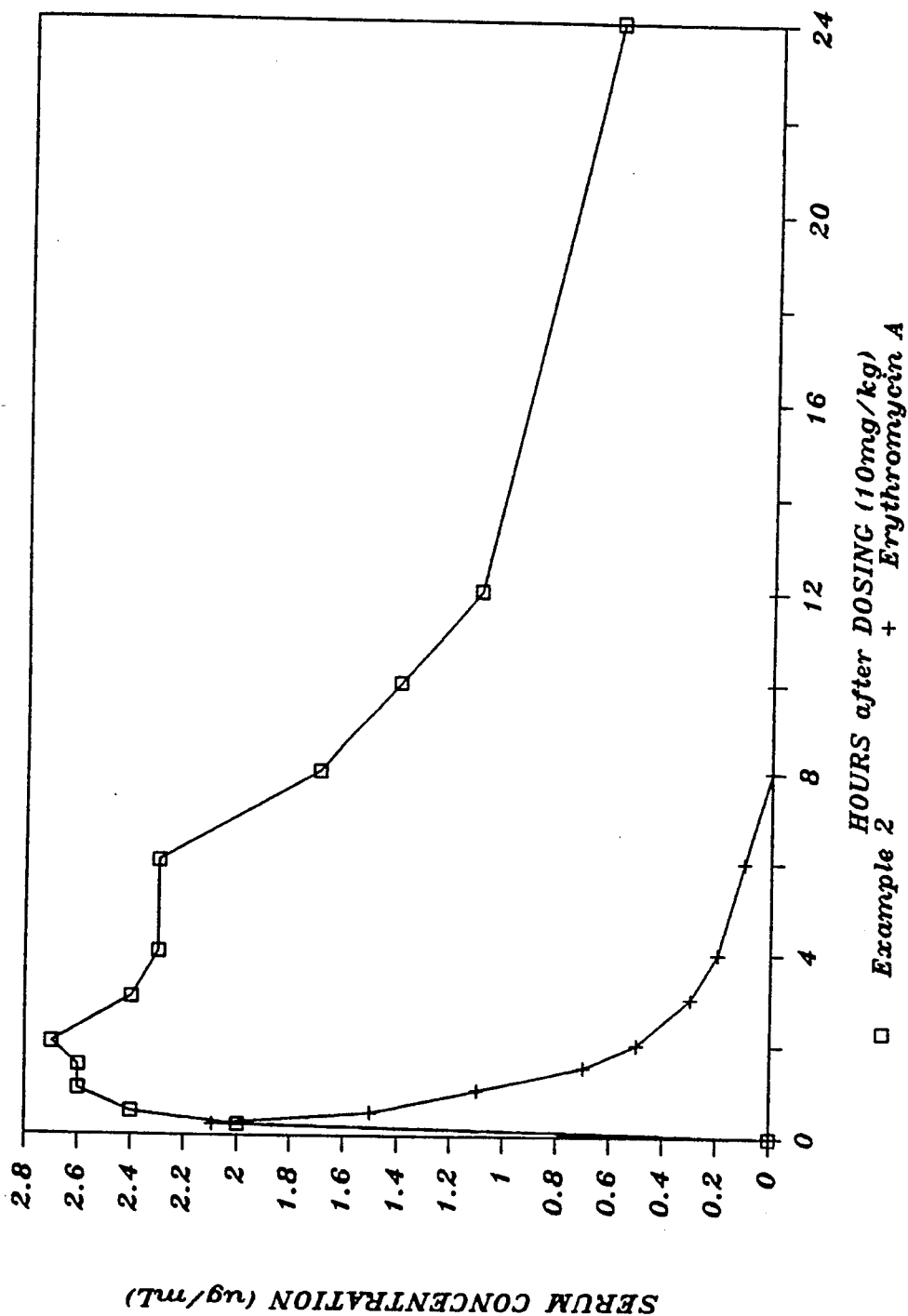

ERYTHROMYCIN A 11,12-CARBONATES AND METHOD OF USE

TECHNICAL FIELD

The invention relates to acid-stable erythromycin derivatives which have improved oral absorption, reduced effects on gastrointestinal motility, increased acid stability and longer serum half-lives.

BACKGROUND ART

Erythromycin A has been used for the treatment of gram positive infections in man for nearly three decades. However, this antibiotic is unreliably absorbed when administered orally, and causes gastrointestinal disturbances such as cramping, nausea, vomiting and diarrhea. It also has a relatively short serum half-life of 2–3 hours in man, and rapidly loses its antibacterial activity in an environment of high acidity (pH 4).

Unreliable absorption of an antibiotic makes control of an infection difficult. Although variation in absorption can be offset by administration of larger doses, higher doses of erythromycin can produce severe gastrointestinal side-effects, as has become apparent from recent clinical studies on intravenous administration of erythromycin lactobionate.

Because of the short serum half-life of erythromycin, administration of three to four doses of antibiotic per day are usually necessary to maintain effective blood levels. It would be desirable to administer the antibiotic only once or twice per day to make patient compliance easier.

Finally, the sensitivity of erythromycin to acid requires carefully designed dosage forms to ensure protection from stomach acidity, yet the antibiotic formulation must efficiently release erythromycin in a less acidic environment, such as the intestine.

It has now been found that certain novel compounds incorporating chemical modifications of both the cladinose sugar and the macrolide ring of erythromycin overcome the above-mentioned problems.

BRIEF DESCRIPTION OF THE DRAWING

The drawing (FIG. 1) is a graph illustrating the results of one experiment in which the blood levels of a compound of this invention were compared with blood levels of erythromycin A of the prior art following oral administration.

DISCLOSURE OF THE INVENTION

Disclosed herein are erythromycin derivatives of the formula:

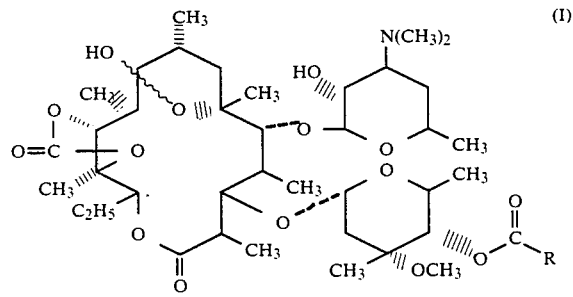

wherein R is lower alkyl, aryl, alkenyl, aryl halide, alkylamino, hydroxyalkyl and furanyl, and pharmaceutically acceptable salts thereof. By modifying the cladinose moiety and the macrolide ring to form a carbonate ester derivative the absorption efficiency is significantly improved and gastrointestinal spasms are virtually eliminated relative to erythromycin.

The terms "alkyl" and "alkenyl" are used herein to mean straight and branched chain saturated and unsaturated radicals, respectively, including, but not limited to, methyl, ethyl, ethenyl, n-propyl, isopropyl, 2-propenyl, n-butyl, sec-butyl, isobutyl, tert-butyl, 1-, 2-, or 3-butenyl, n-nonenyl and the like.

By "aryl" and "aryl halide" herein is meant a substituted or unsubstituted aromatic ring group, the latter being substituted with a halogen, i.e., chloro-, fluoro-, iodo-, and bromo- substituted. These groups include, but are not limited to benzyl, alpha- or beta-naphthylmethyl, chlorophenyl, trifluorophenyl, nitrobenzyl, alkoxybenzyl, and the like.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

The compounds of the present invention can be used in the form of salts derived from inorganic or organic acids. Among the more common salts and esters of erythronolide antibiotics are the estolate (propionate lauryl sulfate salt), ethyl succinate, gluceptate (glucoheptonate), lactobionate, stearate, and hydrochloride forms. Other acid salts used in the pharmaceutical arts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glycerophosphate, hemisulfate, heptonate, hexanoate, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, basic nitrogen-containing groups can be quaternized with such agents as lower alkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of formula I, are synthesized in high yield by the method discussed herein. Erythromycin A is converted to erythromycin A 11,12-carbonate-6,9-hemiketal by the method of Murphy, et. al., U.S. Pat. No. 3,417,077, issued in 1968. The 2'-position is protected by acetylation using acetic anhydride and a proton acceptor such as sodium bicarbonate or triethylamine in an inert solvent such as methylene chloride or acetonitrile. The 2'-acetylerythromycin A 11,12-carbonate-6,9-hemiacetal can be purified by crystallization from an inert solvent such as diethyl ether or ethyl acetate. The 4''-position can then be acylated with a variety of acids using any one of a variety of acylation methods. In the case of 4''-acetylation, reaction of 2'-acetylerythromycin A 11,12-carbonate-6,9-hemiacetal with acetic anhydride in an inert solvent such as acetonitrile or methylene chloride and in the presence of an acylation catalyst such as pyridine or 4-dimethylaminopyridine yields 2′,4″-diacetylerythromycin A 11,12-carbonate- 6,9-hemiacetal. Removal of the 2′-acetyl group is then accomplished by methanolysis for three days at room temperature to provide the desired 4″-acetylerythromycin A 11,12-carbonate-6,9-hemiketal. These reactions are illustrated in the following reaction scheme.

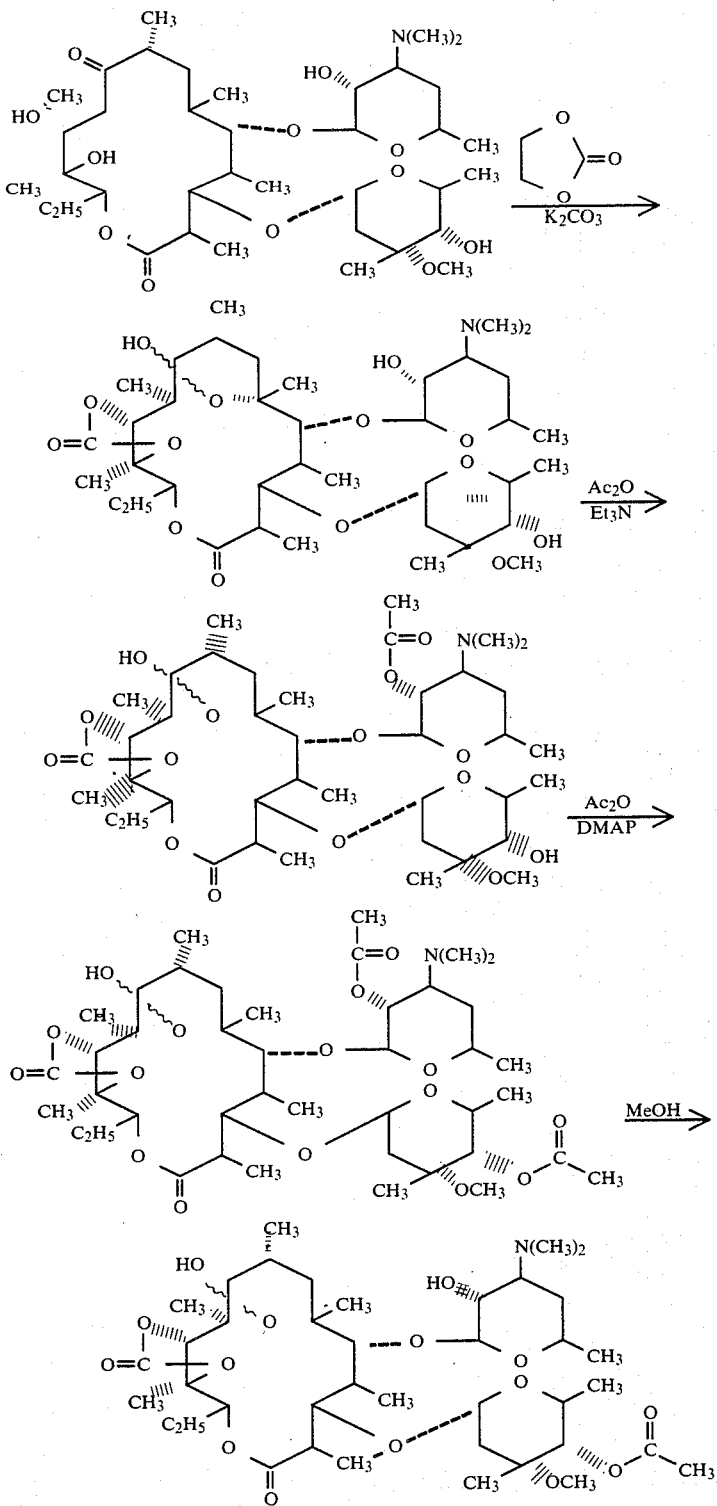

The compounds of formula I are potent antibiotics. Minimum inhibitory concentrations (MICs) are always less than 5 ug/mL and in most cases are less than 1 ug/mL for the following organisms:
Staphylococcus aureus ATCC 6538P
Staphylococcus aureus CMX 686b

*Staphylococcus aureus* 45
*Staphylococcus aureus* 45 RAR2
*Staphylococcus epidermidis* 3519
*Lactobacillus casei* ATCC 7469
*Streptococcus faecium* ATCC 8043
*Streptococcus bovis* A5169
*Streptococcus agalactiae* CMX 508
*Streptococcus pyogenes* EES 61
*Sarcina lutea* 9341
*E. Coli* SS These MICs are higher than the MICs for erythromycin A. However, the improved oral absorption, increased acid stability, and longer half-lives of these compounds outweigh this slight in vitro deficit and make these compounds functionally superior to erythromycin A, as shown in in vivo tests, summarized in Table I, which model clinical performance.

TABLE I

| | In Vivo Efficacy vs. *Staph. aureus* 10649 (100–1000 LD$_{50}$s) | | |
|---|---|---|---|
| | Compound | ED$_{50}$ mg/kg | |
| Model | Number | Subcutaneous | Oral (milk) |
| Acute Mouse | 1 | 6 | 81 |
| Protection | | 9 | 52 |
| | 2 | 15 | 69 |
| | 3 | 30 | 100 |
| | 4 | 27 | 40 |
| | 5 | 34 | 65 |
| | 6 | 35 | 34 |
| Chronic | 1 | — | 200 |
| Abscess | 7 | — | 36 |

Compounds reported in Table I
1. erythromycin A
2. erythromycin A 11,12-carbonate-6,9-hemiacetal
3. 4"-acetylerythromycin A
4. 4"-acetylerythromycin A 11,12-carbonate-6,9-hemiketal HCl salt
5. 4"-propionylerythromycin A 11,12-carbonate-6,9-hemiketal HCl salt
6. 4"-isobutyrylerythromycin A 11,12-carbonate-6,9-hemiketal HCl salt
7. 4"-acetylerythromycin A 11,12-carbonate-6,9-hemiacetal free base The data in Table I illustrate that the oral activity of the compounds of this invention exceeds that of erythromycin A. It should also be noted that this oral activity data was obtained with mice pretreated with milk, which suppresses gastric acid secretion, so that the relative instability of erythromycin A in acid media had less effect on the results. Also, erythromycin A 11,12-carbonate-6,9-hemiacetal, which is significantly more acid-stable than erythromycin A, can be seen to be more active subcutaneously than orally, further indicating that acid stability alone does not account for the the entire improvement in oral activity. Thus, the improved oral activity of the compounds of formula I can be attributed to improved gastrointestinal absorption of these compounds.

The serum half-lives of the new compounds have been measured in both rats and dogs (t$_{0.5}$=2–3 hours in rats, 8–12 hours in dogs). In both species the half lives are 2 to 4-fold longer than the half-life of erythromycin A. In one experiment, 4"-acetylerythromycin A 11,12-carbonate of this invention was administered orally as a solution of a buffered salt in water to three beagle dogs at a dosage of 10.0 mg/kg. Similarly, erythromycin A was administered to other dogs at an equal dosage. Serum concentrations of the administered drug were determined hourly over the 24 hours following administration. The results are depicted in FIG. 1. The results indicate a higher peak blood level and a markedly longer half life for the compound of this invention, in comparison to erythromycin A of the prior art.

The longer half-lives of the compounds of this invention provide another advantage over erythromycin, as demonstrated in the chronic abscess model. In this model, sustained blood levels of antibiotic will prevent reinfection by the organism at the abscess site after the last treatment. The new compounds show activity which is clearly superior to erythromycin in this test.

The compounds of this invention have been tested for gastrointestinal stimulating activity in a dog model at 8 mg/kg intravenously. Contractions in the gut were recorded with surgically implanted strain gauges. The contractile or motility index was determined according to the method of Jacoby, et al., as described in "Gastrointestinal Actions of Metoclopramide," *Gastroenterology*, Vol. 52, No. 4 (1967), pp. 676–684 by giving a numerical score to the height of each recorded contraction in the one hour periods before and after administration of the test compound.

Administration of erythromycin A lactobionate at 2 mg/kg intravenously resulted in pronounced stimulation of the stomach, duodenum, jejunum and ileum. Administration of 4"-acetylerythromycin A 11,12-carbonate-6,9-hemiacetal at the higher dose of 8 mg/kg intravenously resulted in negligible apparent stimulation of the gastrointestinal tissues. The contractile index for the test compounds erythromycin A lactobionate and 4"-acetylerythromycin A 11,12-carbonate-6,9-hemiacetal is shown in Table II:

TABLE II

| | Contractile Index | |
|---|---|---|
| Tissue | 2 mg/kg Erythromycin Lactobionate | 8 mg/kg 4"-acetyl erythromycin A-11,12-carbonate-6,9-hemiacetal* |
| Stomach | 162 | 6 |
| Duodenum | 407 | 58 |
| Jejunum | 82 | 0 |
| Ileum | 3 | 2 |

*Average of two experiments.

This illustrates that the compounds of this invention are devoid of or have significantly less gastrointestinal stimulation than erythromycin A at this dosage level.

The compounds of this invention can be better understood in connection with the following non-limiting examples.

EXAMPLE 1

4"-Acetylerythromycin A 11,12-carbonate-6,9-hemiacetal

A mixture of 100.5 g (0.137 mole) of erythromycin A and 50 g (0.362 mole) of potassium carbonate (K$_2$CO$_3$) in 350 mL of benzene was heated to reflux and 110.9 g (1.259 mole) of ethylene carbonate in 250 mL of benzene was added dropwise during one hour. The mixture was refluxed an additional two hours and then was cooled to ambient temperature. The reaction mixture was washed with 800 mL of 10% aqueous K$_2$CO$_3$ solution, three 500 mL portions of 5% sodium chloride (NaCl) solution, and finally with 500 mL of water. The benzene layer was dried over sodium sulfate (Na$_2$SO$_4$) and was filtered. The benzene was removed using a rotary evaporator and water bath at 40° C. The residue was dried in a vacuum at 23° C. for 18 hours to give 107.8 g of crude erythromycin A 11,12-carbonate-6,9-hemiacetal as a glass.

To effect 2'-acetylation the foregoing product was dissolved in 1.2 liter of methylene chloride (CH$_2$Cl$_2$) and 50.5 g of K$_2$CO$_3$ was added, followed by 98 mL of acetic anhydride. The reaction was complete after stirring for 2.5 hours at ambient temperature. The salts were removed by filtration and the CH$_2$Cl$_2$ was evaporated under vacuum. The residue was dissolved in 1.2 liter of ethyl acetate and was washed with three 1.0 liter portions of 10% aqueous K$_2$CO$_3$. The solvent was dried over Na$_2$SO$_4$, was filtered and evaporated in vacuo at 40° C. The product was dried in a vacuum oven at 23° C. for 20 hours to yield 109.3 g of crude product as a colorless glass. The product was purified by crystallization from 250 mL of diethyl ether at 0° to 5° C. The crystals were isolated and dried giving 69.0 g (0.086 mole) of the title compound; m.p. 205°–207° C.

Analysis Calcd. for C$_{40}$H$_{67}$NO$_{15}$ (801.97):
C, 59.91; H, 8.42; N, 1.75.
Found: C, 59.22; H, 8.43; N, 1.69.

In 110 mL of acetonitrile were dissolved 5 g (6.242 mmol) of 2'-acetylerythromycin A 11,12-carbonate-6,9-hemiacetal, 2.0 mL of triethylamine, 140 mg of 4-dimethylaminopyridine, and 1.2 mL (12.78 mmol) of acetic anhydride. The reaction mixture was kept at 23° C. and was monitored by thin layer chromatography (E. Merck, Darmstadt: precoated the plates, silica gel 60 F-254, developing solvent acetonitrile (CH$_3$CN): concentrated NH$_4$OH (10:0.2). After 20 hours the solvent was evaporated in vacuo. The residue was dissolved in 100 mL of benzene and the mixture was washed with two 25 mL portions of 5% phosphate buffer (pH 6.5) and two 50 mL portions of 4% aqueous sodium carbonate (NaHCO$_3$) solution. The benzene layer was dried over Na$_2$SO$_4$ and was evaporated in vacuo. The resulting colorless foam consisting of 2',4''-diacetylerythromycin A 11,12-carbonate-6,9-hemiacetal was dissolved in 75 mL of methanol and was stored at 23° C. After three days, hydrolysis of the 2'-acetyl ester was complete as seen by thin layer chromatography and the methanol was evaporated in vacuo. The residue was dissolved in 100 mL of benzene and washed first with 4% aqueous NaHCO$_3$ and then with water. The benzene layer was dried over Na$_2$SO$_4$ and was evaporated in vacuo to give 3.90 g (4.863 mmol) of 4''-acetylerythromycin A 11,12-carbonate-6,9-hemiacetal as a colorless glass. The product was dried for 18 hours at 78° C. and 2 torr.

Analysis Calcd. for C$_{40}$H$_{67}$NO$_{15}$ (801.978):
C, 59.91; H, 8.42; N, 1.75.
Found: C, 60.13; H, 8.35; N, 1.53.
IR (CDCl$_3$): V max=1738 and 1800 cm$^{-1}$;
'H-NMR (CDCl$_3$): δ=2.12 (s, 3H), 2.28 (s, 6H), 3.33 (s, 3H) ppm.

EXAMPLE 2

4''-Acetylerythromycin A 11,12-carbonate-6,9-hemiacetal hydrochloride salt

A mixture of 4.697 g (5.86 mmol) of 4''-acetylerythromycin A 11,12-carbonate-6,9-hemiacetal and 313 mg (5.85 mmol) of ammonium chloride was dissolved in 75 mL of methanol. The solvent was evaporated in vacuo and the resulting amorphous powder was dried in a vacuum at room temperature for 48 hours.

Analysis Calcd. for C$_{40}$H$_{68}$ClNO$_{15}$ (838.439):
C, 57.30; H, 8.17; N, 1.67; Cl, 4.23.
Found: C, 57.43; H, 8.17; N, 1.62; Cl, 4.52.
IR (CDCl$_3$): V max=1740 and 1800 cm$^{-1}$;
'H-NMR (CDCl$_3$): δ=2.11 (s, 3H), 2.88 (s, 6H), 3.31 (s, 3H) ppm.

EXAMPLE 3

4''-Propionylerythromycin A 11,12-carbonate-6,9-hemiacetal hydrochloride salt

Following the procedure of Examples 2 and 3, but substituting propionic anhydride for acetic anhydride, 4.024 g (5.018 mmol) of 2'-acetylerythromycin A 11,12-carbonate-6,9-hemiacetal was converted to 3.14 g (3.683 mmol) of 4''-propionylerythromycin A 11,12-carbonate-6,9-hemiacetal hydrochloride salt.

Analysis Calcd. for C$_{41}$H$_{70}$ClNO$_{15}$ (852.466):
C, 57.77; H, 8.28; N, 1.64; Cl, 4.16.
Found: C, 57.14; H, 8.28; N, 1.81; Cl, 4.53.
IR (CDCl$_3$): V max=1742 and 1801 cm$^{-1}$.
'H-NMR (CDCl$_3$): δ=2.88 (s, 6H) and 3.31 (s, 3H) ppm.

EXAMPLE 4

4''-Isobutyrylerythromycin A 11,12-carbonate-6,9-hemiacetal hydrochloride salt

A solution of 4.015 g (5.006 mmol) of 2'-acetylerythromycin A 11,12-carbonate-6,9-hemiacetal and 2.149 g (17.59 mmol) of 4-dimethylaminopyridine in 30 mL of MeCl$_2$ was cooled in an ice bath and while stirring 1.32 mL (12.60 mmol) of isobutyryl chloride was added. The ice bath was removed after 30 minutes and thin layer chromatography (developing solvent CH$_3$CN:concentrated NH$_4$OH (10:0.2)) after 2 hours showed the reaction to be complete. The reaction mixture was cooled in an ice bath and 0.9 mL (8.11 mmol) of N-methylpiperazine was added to consume the excess acid chloride. One hour later the reaction mixture was concentrated in vacuo and the concentrate was dissolved in 150 mL of benzene. The benzene was washed with two 50 mL portions of water, three 50 mL portions of 5% phosphate buffer (pH 6.5), two 50 mL portions of a 9 to 1 mixture of 4% aqueous NaHCO$_3$ and concentrated NH$_4$OH and finally with 50 mL of water. The benzene was dried over Na$_2$SO$_4$ and was removed by evaporation in vacuo. The product, 2'-acetyl-4''-isobutyrylerythromycin A 11,12-carbonate-6,9-hemiacetal, was dried at 23° C. for 18 hours (2 torr) to yield 3.456 of a colorless glass.

Analysis Calcd. for C$_{44}$H$_{73}$NO$_{16}$ (872.070):
C, 60.60; H, 8.44; N, 1.61.
Found: C, 60.92; H, 8.33; N, 1.44.
IR (CDCl$_3$): V max=1740 and 1800 cm$^{-1}$
'H-NMR (CDCl$_3$): δ=2.07 (s, 3H), 2.27 (s, 6H) and 3.34 (s, 3H) ppm.

A solution of 3.30 g of 2'-acetyl-4''-isobutyrylerythromycin A 11,12-carbonate-6,9-hemiacetal in 75 mL of methanol was stored at 23° C. for three-days. The hydrolysis product was isolated by evaporation of the solvent in vacuo and the residue was dried overnight at 50° C. in a vacuum oven (15 torr) to give 4''-isobutyrylerythromycin A 11,12-carbonate-6,9-hemiacetal. This material was converted to the corresponding hydrochloride salt by the method of Example 3. The salt was dried at 50° C. in a vacuum oven for 18 hours to yield 3.02 g of an amorphous powder.

Analysis Calcd. for $C_{42}H_{72}ClNO_{15}$ (866.493):
C, 58.22; H, 8.38; N, 1.62; Cl, 4.09.
Found: C, 57.62; H, 8.34; N, 1.65; Cl, 3.94.
IR ($CDCl_3$): V max=1740 and 1800 cm$^{-1}$
'H-NMR ($CDCl_3$): δ=2.87 (s, 6H) and 3.31 (s, 3H) ppm.

EXAMPLE 5

2'-Acetyl-4"-N-CBZ-sarcosyl erythromycin A 11,12-carbonate-6,9-hemiacetal

A mixture of 4.034 g (5.030 mmol) of 2'-acetylerythromycin A 11,12-carbonate-6,9-hemiacetal, 2.310 g (10.348 mmol, 2.057 equiv) of N-CBZ sarcosine and 0.614 g of 4-dimethylaminopyridine was dissolved in 100 mL of dry $MeCl_2$. Then, 0.83 mL (10.348 mmol) of pyridine and 1.444 g (7.000 mmol, 1.39 equiv) of dicyclohexylcarbodiimide (DCC) were added.

After 18 hours at 0° C. the precipitate of DCU was removed by filtration and was washed with small portions of solvent. The combined filtrate was concentrated to near dryness using a rotary evaporator and $H_2O$ bath at 40° C. The residue was dissolved in 150 mL of benzene and was washed with 50 mL of $H_2O$, two 25 mL portions of 5% pH 6.5 phosphate buffer, three 50 mL portions of a 9 to 1 mixture of 4% $NaHCO_3$; conc $NH_4OH$; and finally with 50 mL $H_2O$. The benzene was dried over $Na_2SO_4$ was filtered and was evaporated with a rotary evaporator and $H_2O$ bath at 40° C. The residue weighed 4.570 g after drying for 18 hours at 50° C. in a vacuum oven.

This residue was chromatographed on a 200 g column of silica gel prepared in $CH_3CN$ and equilibrated with 1.0 L of $CHCl_3$:50% $CH_3CN$ (eluent). The total crude product was put on the column in several mL of eluent and column fractions were analyzed by TLC.

Fractions 65-110 were combined and the solvent was evaporated to give 3.070 g of white glass.

Analysis Calcd. for $C_{51}H_{78}N_2O_{18}$ (1007.193):
C, 60.82; H, 7.81; N, 2.78.
Found: C, 61.07; H, 7.77; N, 2.70.
IR (5% $CDCl_3$): V max=1705, 1745, 1755 sh, 1800, 3530 cm$^{-1}$.

EXAMPLE 6

Preparation 4"-N-CBZ-sarcosyl erythryomycin A 11,12-carbonate-6,9-hemiacetal

The sample 2'-acetyl-4"-CBZ sarcosyl erythromycin A 11,12-carbonate-6,9-hemiacetal was dissolved in 75 mL of MeOH and was allowed to stand at 23° C. over the week end. The reaction was complete by TLC at that point and the solvent was removed with a rotary evaporator and $H_2O$ bath at 40° C.

The sample was dried in a vacuum oven at 50° C. for 18 hours to give 3.224 g of product as a white glass.

Analysis Calcd. for $C_{49}H_{76}N_2O_{17}$ (965.155):
C, 60.98; H, 7.94, N, 2.90.
Found: C, 61.11; H, 8.10; N, 2.78.
IR (5% $CDCl_3$): V max=1705, 1760, and 1800 cm$^{-1}$.

EXAMPLE 7

4"-N,N-dimethylglycylerythromycin A 11,12-carbonate 6,9-hemiacetal monohydrochloride salt Catalytic debenzylation and N-methylation was done in two runs using a Parr shaker.

Run I:

0.601 g 4"-N-CBZ-sarcosylerythromycin A 11,12-carbonate-6,9-hemiacetal
0.300 g 20% Pd/c (wet)
100 mL MeOH
37% Formalin (0.5 mL)

Run II:

2.36 g 4"-N-CBZ-sarcosylerythromycin A 11,12-carbonate-6,9-hemiacetal
1.2 g 20% Pd/c (wet)
MeOH (250 mL)
37% Formalin (3.65 mL)

After filtration of catalyst and evaporation of the methanol, Runs I and II were combined in 100 mL of benzene and were washed with three 30 mL portions of a mixture of 4% $NaHCO_3$ (9 parts): conc $NH_4OH$ (1 part). The benzene was dried over $Na_2SO_4$ and was evaporated to give 2.377 g product as a white glass after drying in a vacuum oven at 23° C. for 3 days.

A 2.178 g (2.577 mmol) sample of 4"-N,N-dimethylglycylerylhromycin A 11,12-carbonate-6,9-hemiacetal was mixed with 137.6 mg (2.572 mmol) of ammonium chloride and the mixture was twice dissolved in MeOH and evaporated to remove ammonia. A 2.176 sample of the salt was obtained.

Analysis Calcd. for $C_{42}H_{73}ClN_2O_{15}$ (881.508):
C, 57.23; H, 8.35; N, 3.18, Cl, 4.02.
Found: C, 56.70; H, 8.57; N, 2.88; Cl 4.60.
IR ($CDCl_3$): V max=1750 and 1801 cm$^{-1}$.
'H-NMR ($CDCl_3$): δ=2.86 (S, 6H), 2.42 (S, 6H) and 3.31 (S, 3H) ppm.

EXAMPLE 8

2'-acetyl-4"-N-CBZ-L-prolylerythromycin A 11,12-carbonate 6,9-hemiacetal

A mixture of 8.005 g (9.982 mmol) of 2'-acetylerythromycin A 11,12-carbonate-6,9-hemiacetal, 1.178 g (9.642 mmol) of 4-dimethyaminopyridine and 11.232 g (45.05 mmol) of N-CBZ-L-proline was dissolved in 160 mL dry $CH_2Cl_2$ and the mixture was cooled in an ice bath to 0-5° C. Then, 6.190 g (30.00 mmol) of DCC was added and the reaction mixture was stored at 0-5° C. for 72 hours.

The mixture was filtered to remove DCU and the filtrate and washings were combined and concentrated to near dryness using a rotary evaporator and $H_2O$ bath at 40° C. The residue was dissolved in 150 mL of benzene and was washed with three 50 mL portions of 5% phosphate buffer at pH 6.5, four 50 mL portions of a 9 to 1 mixture of 4% Aq $NaHCO_3$ and conc. $NH_4OH$. The benzene was dried over $Na_2SO_4$, was filtered and was concentrated to give 11.088 g of white foam, after drying 18 hr @ 23° in a vac. oven.

A 200 g column of silica gel was prepared in $CH_3CN$ and was conditioned with 1.0 l of $CHCl_3$: 50% $CH_3CN$ (eluent). The column was packed and the total crude product was put on the column in several mL of eluent.

Fractions were analyzed by TLC and appropriate fractions were combined and were evaporated to dryness. The product isolated as a white foam weighing 8.433 g after drying 2 days in a vacuum oven at 23° C.

Analysis Calcd. for $C_{53}H_{80}N_2O_{18}$ (1033,231):
C, 61.61; H, 7.80; N, 2.71.
Found: C, 61.44, H, 7.73; N, 2.92.
IR ($CDCl_3$): V max=1705, 1748, 1800, 3530 cm$^{-1}$.

EXAMPLE 9

4''-N-CBZ-L-prolylerythromycin A carbonate-6,9-hemiacetal

An 8.333 g sample of 2'-acetyl-4''-N-CBZ-L-prolylerythromycin A 11,12-carbonate-6,9-hemiacetal was dissolved in 75 mL of MeOH and was allowed to stand at 23° C. for 72 hr. A TLC showed no 2'-acetate left at that time. The methanol was removed with a rotary evaporator and H$_2$O bath at 40° C. to give 7.672 g of product.

Analysis Calcd. for C$_{51}$H$_{78}$N$_2$O$_{17}$ (991.194):
C, 61.80; H, 7.93; N, 2.83.
Found: C, 61.73; H, 8.00; N, 3.05.
IR (CDCl$_3$): V max = 1702, 1750, and 1800 cm$^{-1}$.

EXAMPLE 10

4''-L-prolylerythromycin A carbonate-6,9-hemiacetal monohydrochloride salt

A 3.71 g sample of 4''-N-CBZ-L-prolylerythromycin A 11,12-carbonate-6,9-hemiacetal was dissolved in 200 mL of methanol and 1.5 g of 20% Pd-C (dry) was added. The mixture was hydrogenated at 3 atm pressure of H$_2$ on a Parr shaker apparatus. After 2 hours the catalyst was removed by filtration and the filtrate was concentrated to near dryness with a rotary evaporator and H$_2$O bath (ca. 40° C.). The residue was dissolved in 100 mL of benzene and was washed with three 33 mL portions of a 9:1 mixture of 4% NaHCO$_3$: conc NH$_4$OH. The benzene was dried over NaSO$_4$, filtered and evaporated to give 2.853 g of 4''-L-prolylerythromycin A 11,12-carbonate-6,9-hemiacetal as a white glass.

A 2.726 g (3.181 mmol) sample of 4''-L-prolylerythromycin A 11,12-carbonate-6,9-hemiacetal was mixed with 165.0 mg (3.085 mmol) of NH$_4$Cl and the mixture was twice dissolved in MeOH and concentrated to dryness.

Analysis Calcd. for C$_{43}$H$_{73}$ClN$_2$O$_{15}$ (893.519):
C, 57.80; H, 8.24; N, 3.14; Cl, 3.97.
Found: C, 57.52; H, 8.23; N, 2.62; Cl, 4.40.
IR (CDCl$_3$): V max = 1800 and 1745 cm$^{-1}$.
'H-NMR (CDCl$_3$): δ = 2.63 (S, 6H) and 3.31 (S, 3H) ppm.

EXAMPLE 11

2'-acetyl-4''-N-CBZ-L-alanylerythromycin A 11,12-carbonate-6,9-hemiacetal

A mixture consisting of 4.032 g (5.028 mmol) of 2'-acetylerythromycin A 11,12-carbonate-6,9-hemiacetal, 0.906 g (7.419 mmol) of 4-dimethylaminopyridine, and 5.052 g (22.631 mmol) of N-CBZ-L-alanine was dissolved in 100 mL of dry CH$_2$Cl$_2$ and was cooled to −23° C. in a Dry-ice; CCl$_4$ bath. Then, 3.159 g (15.310 mmol) of DCC was added and the mixture was kept at −25° C. for three days.

The precipitated DCU was removed and the filtrate concentrated to near dryness. The residue was dissolved in 150 mL of benzene and was washed with 50 mL H$_2$O, three 50 mL portions of pH 6.5 phosphate buffer (5%), three 50 mL portions of 9:1 mixture of 4% Aq NaHCO$_3$: conc NH$_4$OH and finally with 50 mL of water. The benzene was dried over Na$_2$SO$_4$ (1 g Silica Gel added) and the mixture was filtered. The benzene was evaporated at 40° C. giving 5.3 g of crude product after drying 50° C. in a vacuum oven overnight.

A 200 g column of silica gel was prepared in CH$_3$CN and was equilibrated with 1.0 l of CHCl$_3$: CH$_3$CN (50/50). The crude sample (5.3 g) was put on the column in several mL of eluent. The fractions were analyzed by TLC and appropriate tubes were combined and the solvent evaporated.

The residue (a white glass) was dried 50° C. for 18 hr in a vacuum oven to give 3.729 g of 2'-acetyl-4''-N-CBZ-L-alanylerythromycin A 11,12-carbonate-6,9-hemiacetal (74% yield).

Analysis Calcd. for C$_{51}$H$_{78}$N$_2$O$_{18}$ (1007.193):
C, 60.82; H, 7.81; N, 2.78.
Found: C; 60.97; H, 7.74; N, 2.60.
IR (CDCl$_3$): V max = 1730 sh; 1745; 1800, 3530 (OH), and 3440 (NH) cm$^{-1}$.

EXAMPLE 12

4''-N-CBZ-L-alanylerythromycin A 11,12-carbonate-6,9-hemiacetal

The product from Example 12 was dissolved in 80 mL of MeOH and was allowed to stand at 23° C. for 72 hours. After 72 hr, TLC showed complete hydrolysis.

The solvent was evaporated and the white glass obtained was dried for 18 hours at 50° C. in a vacuum oven to give 3.614 g of 4''-N-CBZ-L-alanylerylhromycin A 11,12-carbonate-6,9-hemiacetal.

Analysis Calcd. for C$_{49}$H$_{76}$N$_2$O$_{17}$ (965.155):
C, 60.98; H, 7.94; N, 2.90.
Found: C, 60.87; H, 7.90; N, 2.89.
IR (CDCl$_3$) V max = 1730, 1800, 3440, and 3530 cm$^{-1}$.

EXAMPLE 13

4''N,N-dimethyl-L-alanylerythromycin A 11,12-carbonate-6,9-hemiacetal monohydrochloride salt To a solution of 3.33 g of 4''-N-CBZ-L-alanylerythromycin A 11,12-carbonate-6,9-hemiacetal in 300 mL of methanol was added 0.57 g of 20% Pd-C (dry) and the mixture was shaken at 3 atm. H$_2$ pressure in a Parr apparatus for 2 hours. The catalyst was removed by filtration and the methanol was evaporated to give 2.56 g of a grey residue. The residue was dried in a vacuum oven at 23° C. overnight.

The residue was dissolved in 95 mL methanol and 50 mL 37% formalin (CH$_2$O) and 1.25 g 20% Pd-C (wet) were added. The mixture was shaken at 3 atm. H$_2$ pressure for 3 hours. The catalyst was removed by filtration and the methanol was concentrated to near dryness with a rotary evaporator and water bath (40° C.). The residue was dissolved in 100 mL benzene and was washed with three 30 mL portions of a 9:1 mixture of 4% NaHCO$_3$: conc NH$_4$OH. The benzene was dried over Na$_2$SO$_4$, was filtered and was evaporated to give 2.511 g of product. A 2.375 g (2.765 mmol) sample of 4''-N,N-dimethyl-L-alanylerythromycin A 11,12-carbonate-6,9-hemiacetal was mixed with 143.6 mg (2.685 mmol) of NH$_4$Cl and the mixture twice dissolved in MeOH and evaporated to dryness.

Analysis Calcd. for C$_{43}$H$_{75}$Cl N$_2$O$_{15}$ (895.535):
C, 57.67; H, 8.44; N, 3.13, Cl, 3.96.
Found: C, 57.22, H, 8.39; N, 2.68; Cl, 4.59.
IR (CDCl$_3$): V max = 1745 and 1800 cm$^{-1}$.
NMR (CDCl$_3$): δ = 2.45 (s, 6H), 2.77 (s, 6H) and 3.31 (s, 3H) ppm.

EXAMPLE 14

4''-N-methyl-L-prolylerythromycin A 11,12-Carbonate-6,9-hemiacetal monohydrochloride salt To a solution of 3.84 g of the product of Example 10 in 300 mL of methanol was added 6.0 mL of 37% formalin and 0.95 g of 20% Pd-C (dry). The mixture was shaken in a Parr apparatus for 3 hours at 3 atm $H_2$ pressure. The catalyst was removed by filtration and the methanol was evaporated using a rotary evaporator and a water bath at 40° C. The residue was dissolved in 100 mL of benzene and was washed with three 33 mL portions of 9:1 mixture of 4% Aq $NaHCO_3$ and conc. $NH_4OH$. The benzene was dried over $Ha_2SO_4$ and evaporated to give 3.123 g of 4''-N-methyl-L-prolylerythromycin A 11,12-carbonate-6,9-hemiacetal as a white glass.

A 2.998 g (3.442 mmol) sample of this product and 179.1 mg (3.348 mmol) of $NH_4Cl$ were dissolved in 50 mL of MeOH and the solvent was evaporated. The residue was redissolved in 50 mL of MeOH and was again concentrated to dryness (40° C). The residue was dried in a vacuum oven at 23° C. for 3 days to give 3.001 g of the desired product.

Analysis Calcd. for $C_{44}H_{75}Cl\ N_2O_{15}$ (907.546); C, 58.28; H, 8.33; N, 3.09; Cl, 3.91.

Found: C, 57.46; H, 8.38; N, 2.73; Cl, 4.21.

IR ($CDCl_3$): V max = 1748 and 1800 $cm^{-1}$.

'H-NMR ($CDCl_3$): $\delta$ = 2.42 (s,3H), 2.82 (s,6H) and 3.31 (s,3H) ppm.

EXAMPLE 15

4''-Benzoyl erythromycin A 11,12-Carbonate-6,9-hemiacetal 5.003 g (6.24 mmol) of 2'-acetyl erythromycin A 11,12-carbonate-6,9-hemiacetal and 3.619 g (29.62 mmol) of 4-dimethylamino pyridine were weighed out and transferred to a 250 mL round bottom flask. Then 125 mL of $CH_2Cl_2$ was added to dissolve the two reagents. 2.9 mL (3.5 g; 24.9 mmol) of benzoyl chloride was then added in one portion. The flask was then fitted with a $CaSO_4$ drying tube and placed in a refrigerator at 0° C. for 3 days. The $CH_2Cl_2$ was evaporated and the residue was taken up in 300 mL of hot ethyl acetate. The resulting slurry was washed twice with 100 mL aliquots of 10% aqueous phosphate buffer (pH 7.0), which washed out the solid residue.

The reaction was then washed twice with 100 mL aliquots of 4% aqueous $NaHCO_3$ solution. The ethyl acetate portion was then dried over anhydrous $Na_2SO_4$, filtered and evaporated under vacuum. The residue recovered weighed 5.937 g.

This residue was dissolved in 150 mL of absolute MeOH and the flask was stoppered. After 3 days, 1.5 g of charcoal was added to the solution which was then stirred for 10 minutes. Solution was then filtered through a celite matt. The filtered solution was evaporated under vacuum at 25° C. The residue was pumped on an oil pump for several hrs., then taken up in 100 mL of benzene and stirred for 20 mins. with 1.0 g of silica gel. The mixture was then filtered by suction using a medium fritt sintered glass funnel. The filtered solution was evaporated under vacuum. The recovered colorless residue had a strong odor similar to that of a benzoate ester. This was removed by silica gel column chromatography using $CH_3CN$ as eluent followed by trituration of chromatographed material with heptane and vacuum oven drying at 45° C.

Wt. of glass recovered was 3.339 g.

'H-NMR ($CDCl_3$): $\delta$ = 2.33(S,6H), 3.38(S,3H), 7.45(t,2H), 7.58(t,1H), and 8.05(d,2H) ppm.

IR ($CDCl_3$): V max = 1799, 1721 $cm^{-1}$.

Analysis Calcd. for $C_{45}H_{69}NO_{15}$ (864.039):
C, 62.55; H, 8.05; N, 1.62.
Found: C, 62.52; H, 8.06; N, 1.75.

EXAMPLE 16

4''-Benzoylerythromycin A 11,12-carbonate-6,9-hemiacetal hydrochloride salt 2.765 g (3.20 mmol) of the product of Example 16 was dissolved in 50 mL of absolute MeOH in a 100 mL round bottom flask.

To the methanol solution was added 0.163 g (3.04 mmol) of $NH_4Cl$. The mixture was stirred at 25° C. for 20 minutes (until $NH_4Cl$ had dissolved). The solution was filtered through a Millipore EH membrane filter. The filtered solution was evaporated under vacuum. The residue obtained was dried in a vacuum oven for 18 hrs. at 47° C.

2.787 g of salt was recovered.

Analysis Calcd. for $C_{45}H_{70}ClNO_{15}$ (900.500):
C, 60.02; H, 7.84; N, 1.56; Cl, 3.94. Found: C, 59.91; H, 7.88; N, 1.52; Cl, 6.42.

EXAMPLE 17

4''-Benzyloxyacetylerythromycin A 11,12-carbonate-6,9-hemiacetal

2'-acetyl erythromycin A (5.007 g, 6.24 mmol), 4-dimethylaminopyridine (0.765 g, 6.26 mmol), diisopropyl ethyl amine (3.26 ml, 18.72 mmol), and benzyloxy acetic acid (3.110 g, 18.72 mmol) were dissolved in 125 mls of methylene chloride in a 250 mL flask equipped with magnetic stir bar. The solution was stirred magnetically while it was cooled to 0° C. in an ice bath. DCC (3.859 g, 18,70 mmol) was then weighed out and added to the cooled, stirring reaction mixture. The flask was fitted with a $CaSO_4$ drying tube. The solution was stirred at 0° C. for 1 hr and then stored overnight at 0° C. After 22 hrs, the reaction was checked by TLC and found to be essentially complete.

The solution was washed twice with 100 mL aliquots of 4% aqueous $NaHCO_3$ solution. The washed reaction solution was then dried over anhyd. $Na_2SO_4$, filtered and evaporated to a thick gummy syrup.

The entire amount of syrup was flash chromatographed on a silica gel column using $CH_3CN$ as the eluting solvent. 4.825 g of pure acetylated product was recovered.

4.02 g of this product was dissolved in 100 mL of absolute MeOH and the solution was allowed to stand at room temperature for 3 days. The reaction was checked by TLC after 3 days and was found to be complete.

The solution was evaporated in vacuo and the recovered residue was pumped on a vacuum pump for several hours. Amount recovered = 3.842 g.

The recovered residue was triturated with heptane and then dried in a vacuum oven overnight at 45° C. Wt. of triturated, dried compound = 3.382 g.

'H-NMR($CDCl_3$): $\delta$ = 2.27(S,6H), 3.31(S,3H), and 7.35(m,5H) ppm.

IR ($CDCl_3$): V max = 1800, 1759, 1745 (shoulder) $cm^{-1}$.

Analysis Calcd. for $C_{47}H_{73}NO_{16}$(908.092):
C, 62.17; H, 8.10; N, 1.54.
Found: C, 61.93; H, 8.16; N, 1.33.

EXAMPLE 18

4''-Benzyloxyacetylerythromycin A 11,12-carbonate-6,9-hemiacetal hydrochloride salt 0.501 g (0.552 mmol) of 4''-benzyloxyacetylerythromycin A 11,12-carbonate-6,9-hemiacetal was dissolved in 15 mL of absolute MeOH. Then 0.028 g (0.524 mmol) of $NH_4Cl$ was added to the MeOH solution. The mixture was stirred for 20 minutes (until $NH_4Cl$ dissolved). The solution was filtered through a Millipore EH filter and the filtered solution was evaporated in vacuo. The residue was taken up in The residue was pumped on a vacuum pump for 3 hrs. and then $CH_3CN$ and the $CH_3CN$ was evaporated under vacuum. The residue was pumped on a vacuum pump for 3 hrs. and then dried overnight in a vacuum oven at 47° C.

515 mgs of the hydrochloride salt was recovered.
Analysis Calcd. for $C_{47}H_{74}ClNO_{16}$ (944.553):
C, 59.77; H, 7.90; N, 1.48; Cl, 3.75.
Found: C, 59.74; H, 7.96; N, 1.37; Cl, 4.18.

EXAMPLE 19

4''-Crotonylerythromycin A 11,12-carbonate-6,9-hemiacetal

2'-Acetylerythromycin A 11,12-carbonate-6,9-hemiketal (4.002 g; 4.99 mmol), DMAP (3.109 g; 25.45 mmol) and crotonic acid (4.337 g; 50.38 mmol) were weighed out and added to a flask where they were then dissolved in 60 mL of $CH_2Cl_2$. Diisopropylethylamine (2.8 ml; 16.1 mmol) was then added to the solution. The solution was allowed to stir and was cooled to 0° C. in an ice bath. Contents of flask were kept as dry as possible using a $CaSO_4$ drying tube. After the solution had cooled, DCC (10.294 g; 49.89 mmol) was added to the solution. After the DCC had dissolved, the flask was kept at 0° C. for 3 days.

A TLC was run on the solution after 3 days which showed the reaction to be complete. The solution was filtered to remove the bulk of the DCU. The filtered solution was then evaporated to a concentrated syrup. This syrup was taken up in $CH_3CN$ and evaporated again. The residue was taken up in 80 mL of $CH_3CN$ and then cooled. More DCU precipitated and this was filtered again. The refiltered solution was evaporated to a concentrated syrup. This syrup was flash chromatographed on a column containing 475 g of Silica gel (40 micron) eluting with $CH_3CN$. 3.603 g of pure 2'-acetyl-4''-crotonyl-erythromycin A 11,12-carbonate-6,9-hemiacetal was recovered as an orange glass.

3.596 g of this product was dissolved in 125 mL of absolute MeOH. The flask was stoppered and the orange solution was allowed to stand at 25° C. for 3 days. After 3 days, the reaction was complete, therefore 2.2 g of charcoal was added and the mixture was stirred for 15 mins, then filtered through a celite matte. The solution was then evaporated and the residue weighed 3.306 g. This was taken up in 100 mL of benzene and treated with 1.6 g of silica gel and then again with 2.0 g of silica gel. The benzene was evaporated to yield 2.684 g of a pale-yellow glassy solid. The glass was redissolved in 100 mL of MeOH. The solution was treated with 1.5 g of charcoal and filtered through a celite matte. The solvent was evaporated in vacuo to yield 2.186 g of a pale yellow glass. The glass was triturated with heptane and dried in a vacuum oven at 45° C., to give 1.740 g. of 4''-crotonylerythromycin A 11,12-carbonate-6,9-hemiacetal.

$^1$H-NMR($CDCl_3$): $\delta = 2.3(S,6H)$ and $3.32(S,3H)$ ppm.
IR ($CDCl_3$): V max = 1718, 1736 (shoulder), and 1797 cm$^{-1}$.
Analysis Calcd. for $C_{42}H_{69}NO_{15}$(828.006):
C, 60.92; H, 8.40; N, 1.69.
Found: C, 61.07; H, 8.23; N, 1.72.

EXAMPLE 20

4''-Crotonylerythromycin A 11,12-carbonate-6,9-hemiacetal hydrochloride salt 1.200 g (1.449 mmol) of the 4''-crotonyl derivative was dissolved in 25 mL of absolute MeOH. To the MeOH solution was added 0.074 g (1.377 mmol) of $NH_4Cl$. The mixture was stirred at 25° C. for 45 minutes. The solution was filtered through a Millipore EH membrane filter. The filtered solution was then evaporated to yield 1.199 g of the salt.

EXAMPLE 21

4''-Glycolylerythromycin A 11,12-Carbonate-6,9-Hemiacetal 2.775 g (3.06 mmol) of 4''-Benzyloxyacetylerythromycin A carbonate-6,9-hemiacetal was hydrogenated in methanol over 20% Pd-C to remove the benzyl group. The reaction was monitored by TLC, and was complete after 4 hrs. The solution was filtered and the catalyst was washed well with MeOH. The filtered reaction solution was refiltered through a Millipore EH membrane filter and the solvent was evaporated under vacuum to yield a colorless glass (1.750 g). The crude compound was chromatographed on a 50×300 mm flash column filled with 275 g of 40 micron silica gel using the eluent system $CH_3CN$:MeOH:$Et_3N$ (10:0.2:0.1). Fractions were collected, combined and evaporated to give 0.577 g of pure product.

$^1$H-NMR ($CDCl_3$): $\delta = 2.29(S,6H)$ and $3.32(S,3H)$ ppm.
IR ($CDCl_3$): V max = 1793, and 1741 cm$^{-1}$.
Analysis Calcd. for $C_{40}H_{67}NO_{16}$(817.967):
C, 58.74; H, 8.26; N, 1.71.
Found: C, 58.77; H, 8.24; N, 1.53.

EXAMPLE 22

4''-Glycolylerythromycin A 11,12-Carbonate-6,9-Hemiacetal Hydrochloride salt 0.551 g (0.67 mmol) of 4''-glycolylerythromycin A 11,12-carbonate-6,9-hemiacetal was dissolved in 20 mL of absolute MeOH.

To the MeOH solution was added 0.034 g (0.64 mmol) of $NH_4Cl$. The mixture was stirred at room temperature for 20 minutes (until all the $NH_4Cl$ had dissolved). The solution was gravity filtered through Whatman #1 paper. The filtered solution was then evaporated to yield 0.540 g of a colorless glassy solid which was the hydrochloride salt.

Analysis Calcd. for $C_{40}H_{68}ClNO_{16}$(854.428):
C, 56.23; H, 8.02; N, 1.64; Cl, 4.15.
Found: C, 56.05; H, 8.04; N, 1.71; Cl, 4.15.

EXAMPLE 23

4''-Phenylacetyl erythromycin A 11,12-carbonate-6,9-hemiacetal 4.001 g (4.99 mmol) of 2'-acetylerythromycin A 11,12-carbonate-6,9-hemiacetal and 0.774 g (6.34 mmol) of DMAP were weighed out and added to a 250 mL RB flask equipped with magnetic stir bar and $CaSO_4$ drying tube. 40 mL of $CH_2Cl_2$ was then added to dissolve the two reagents followed by 0.74 mL (4.26 mmol) of diisopropylethylamine and 1.71 g (12.57 mmol) phenylacetic acid. Another 40 mL of $CH_2Cl_2$ was added to the flask and the drying tube was replaced. The solution was cooled in an ice bath to 0° C. 2.573 g (12.47 mmol) of DCC was then added, followed by another 20 mL of $CH_2CL_2$. The solution was stirred at 0° C. in an ice bath for 45 mins., then allowed to stand at 0° C. for 18 hrs.

After 18 hrs., the solution was filtered to remove the bulk of the DCU. The filtered solution was evaporated and the residue was taken up in 30 mL of hot $CH_3CN$. The solution was cooled in a ice bath for 45 min. More DCU precipitated out and the solution was filtered again. The refiltered solution was evaporated to dryness. 5.6 g of crude product (orange glassy solid) was recovered. This crude material was flash chromatographed on a silica gel column using $CH_3CN$ (neat) as the eluting solvent. This yielded 2.695 g of pure 2'-acetyl-4''-phenylacetyl-erythromycin A 11,12-carbonate-6,9-hemiacetal as a colorless glassy solid.

2.68 g of 2'-acetyl-4''-phenylacetylerythromycin A 11,12-carbonate-6,9-hemiacetal was dissolved in 100 mL of absolute MeOH. The flask was stoppered and the solution was allowed to stand at room temperature for 3 days. The MeOH was evaporated under vacuum and the resulting glassy solid was pumped on an oil pump until dry to yield 2.256 g. of a glass.

'H-NMR ($CDCl_3$): δ=2.29(S,6H), 3.31(S,3H), and 7.31(m,5H) ppm.
IR ($CDCL_3$): V max=1797, 1738 $cm^{-1}$.
Analysis Calcd. for $C_{46}H_{71}NO_{15}$(878.07):
C, 62.92; H, 8.15; N, 1.60.
Found: C, 62.98; H, 8.10; N, 1.50.

EXAMPLE 24

4''-Phenylacetyl-erythromycin A 11,12-Carbonate-6,9-Hemiacetal Hydrochloride Salt 1.956 g (2.23 mmol) of 4''-phenylacetylerythromycin A 11,12-carbonate-6,9-hemiacetal was dissolved in 30 mL of absolute MeOH.

0.113 g (2.12 mmol) of $NH_4Cl$ was weighed out and added to the MeOH solution above. The mixture was stirred for 20 mins. at room temperature (until all $NH_4Cl$ had dissolved). The solution was then gravity filtered through Whatman 2ᵛ paper. The filtered solution was then evaporated in vacuo to obtain a colorless glass which was dried for 20 hrs at 45° C. in a vacuum oven.

EXAMPLE 25

Erythromycin C 11,12; 3'', 4''-Dicarbonate-6,9-hemiacetal

To a mixture of 2.500 g of erythromycin C (ca. 80% pure), 2.868 g of powdered $K_2CO_3$, and 6.754 g of solid ethylene carbonate was added 120 mL of toluene. The reaction mixture was stirred in an oil bath at 50°-60° C. for 2 days.

The reaction mixture was transferred to a separatory funnel and 50 mL toluene was added. The organic layer was washed first with 50 mL $H_2O$, then with three 50 mL portions of 4% aq. $NaHCO_3$. The benzene was dried over $Na_2SO_4$ and was filtered and concentrated with a rotary evaporator (40° C.). The residue was vacuum dried overnight to give 2.586 g of crude product.

A 200 g column of silica gel was prepared in benzene and was conditioned with the éluent solvent system benzene:MeOH:$Et_3N$ (96.4:3.0:0.6).

The crude product was put on the column in several mL of solvent and the column was eluted with the eluent solvent system.

The fractions were analyzed by TLC: (9.5 $CHCl_3$: 0.5 MeOH: 0.2 Conc $NH_4OH$) and appropriate fractions were combined and concentrated to about 100 mL. The organic layer was washed three times with 33 mL aliquots of 4% aq. $NaHCO_3$, was dried over $Na_2SO_4$, and was concentrated to dryness with a rotary evaporator (40° C.). The residue was vacuum dried overnight to give 1.177 g of erythromycin C 11,12:3'', 4''-dicarbonate-6,9-hemiacetal as a glass.

'H-NMR ($CDCl_3$): 2.29(s,6H) ppm.

EXAMPLE 26

Erythromycin C 11,12; 3'',4''-dicarbonate-6,9-Hemiacetal Hydrochloride salt

A 519.2 mg (0.67306 mmol) sample of erythromycin C 11,12: 3'',4''-dicarbonate-6,9-hemiacetal and 34.7 mg (0.65 mmol) of $NH_4Cl$ were dissolved in 25 mL of MeOH and the solvent was evaporated in vacuo at 40° C. The residue was redissolved and re-evaporated from 25 mL of MeOH. The residue was dried 2 hr at 78° C. and 2 torr giving 472 mg of the product as a glass.

IR ($CDCl_3$) V max=1795 and 1732 $cm^{-1}$.
'H-NMR ($CDCl_3$): δ=2.87(s,6H) ppm.
Analysis Calcd. for $C_{38}H_{62}ClNO_{15}$(808.369):
C, 56.46; H, 7.78; N, 1.73; Cl, 4.39.
Found: C, 56.68; H, 7.68; N, 1.55; Cl, 4.47.

EXAMPLE 27

4''-Ethoxycarbonylerythromycin A 11,12-carbonate-6,9-Hemiacetal 5.00 g (6.23 mmol) of 2'-Acetylerythromycin A 11,12-carbonate-6,9-hemiacetal was weighed out and added to a 250 mL RB flask followed by 8.374 g (68.54 mmol) of DMAP and 100 mL of $CH_2Cl_2$. The resulting solution was cooled to −25° C. via $CCl_4$/dry ice bath. Then 5.96 mL (62.29 mmol) of ethyl chloroformate was added to the cooled solution in one portion with stirring. Stirring was continued for 1.5 hrs at −25° C., and then the reaction was allowed to stand at −25° C. for 7 days. After 7 days, there was only a small amount of starting material left. The reaction was warmed to 0° C. and was allowed to stand at 0° C. for 1 day. The reaction was washed twice with 100 mL aliquots of 6% pH 6.0 phosphate buffer and then twice with 100 mL aliquots of 4% aqueous $Na_2CO_3$ solution. The $CH_2Cl_2$ layer was then dried over anhydrous $Na_2SO_4$ and filtered. The dry $CH_2Cl_2$ solution was evaporated under vacuum to yield a glassy solid.

The crude product was flash chromatographed using $CH_3CN$ (neat) on a silica gel column to yield 4.635 g of colorless, odorless glassy material, which was identified as pure 2'-Acetyl-4''-ethoxycarbonyl erythromycin A 11,12-carbonate-6,9-hemiacetal.

4.6 g of 2'-acetyl-4"-ethoxycarbonyl erythromycin A 11,12-carbonate-6,9-hemiacetal was dissolved in 100 mL of absolute MeOH. The flask was stoppered and allowed to stand at room temperature for 3 days. After 3 days, the solution was filtered and then evaporated in vacuo to yield 4.754 g of 4"-ethoxycarbonyl erythromycin A 11,12-carbonate-6,9-hemiacetal as a colorless glass.

'H-NMR (CDCl$_3$): δ=2.28(s,6H) and 3.33(s,3H) ppm.

IR (CCl$_4$): V max=1764, 1749 cm$^{-1}$.

Analysis Calcd. for $C_{41}H_{69}NO_{16}$(831.994):
C, 59.19; H, 8.36; N, 1.68.
Found: C, 58.76; H, 8.19; N, 1.14.

EXAMPLE 28

4"-Ethoxycarbonylerythromycin A
11,12-carbonate-6,9-hemiacetal Hydrochloride Salt 3.223 g (3.87 mmol) of 4"-ethoxycarbonyl erythromycin A 11,12-carbonate-6,9-hemiacetal was dissolved in 75 mL of absolute MeOH. Then 0.197 g (3.68 mmol) of NH$_4$Cl were added and the mixture stirred until NH$_4$Cl dissolved (about 15 min.). The solution was filtered and the MeOH was evaporated to yield 3.359 g of the hydrochloride salt.

EXAMPLE 29

4"-(p-Anisoyl)erythromycin A
11,12-carbonate-6,9-hemiacetal 5.00 g (6.23 mmol) of 2'-Acetylerythromycin A 11,12-carbonate-6,9-hemiacetal and 4.467 g (36.56 mmol) DMAP were dissolved in 100 mL of untreated CH$_2$Cl$_2$. The solution was cooled to 0° C. using an ice bath. After the temperature was obtained, 4.2 ml (31.2 mmol) of p-anisoyl chloride was added to the stirred, cooled solution by means of a glass syringe. The solution was stirred for a few hrs. at 0° C., then allowed to stand at 0° C. for 18 hrs.

After 18 hrs., 4 equivalents of N-methyl piperazine were added to the reaction. The reaction was stirred for 4 hrs. at 0° C. and was then washed twice with 100 mL aliquots of 10% pH 6.3 phosphate buffer followed by two 100 mL aliquots of 4% aqueous NaHCO$_3$ solution. The washed solution was dried over anhydrous Na$_2$SO$_4$, filtered and treated with 2 g of silica gel for 20 min. The mixture was filtered and the filtrate was evaporated to a yellow glassy solid. The yellow glass was flash chromatographed on a silica gel column (50×300 mm) to yield 4.95 g of 2'-acetyl-4"-(p-anisoyl)erythromycin A 11,12-carbonate-6,9-hemiacetal as a colorless glass. This product was dissolved in 100 mL of absolute methanol and after 4 days, the MeOH was evaporated leaving pure 4"-p-anisoyl)erythromycin-11,12-carbonate-6,9-hemiacetal as a colorless glassy solid weighing 4.101 g.

'H-NMR (CDCl$_3$): δ=2.34(s,6H), 3.37(s,3H), 3.87(s,3H), 6.92(d,2H) and 8.00(d,2H) ppm.

IR (CDCl$_3$): V max=1800, 1748, 1715 cm$^{-1}$.

Analysis Calcd. for $C_{46}H_{71}NO_{16}$(894.065):
C, 61.80; H, 8.00; N, 1.57.
Found: C, 61.50; H, 7.81; N, 1.44.

EXAMPLE 30

4"-(p-Anisoyl)erythromycin A
11,12-Carbonate-6,9-Hemiacetal Hydrochloride Salt 2.996 g (3.35 mmol) of 4"-(p-anisoyl) erythromycin A 11,12-carbonate-6,9-hemiacetal was dissolved in 60 mL of absolute MeOH.

170 mg (3.18 mmol) of NH$_4$Cl was added to the MeOH solution and the mixture stirred until dissolved (about 15 min.). The solution was then gravity filtered through Whatman 2$^v$ paper and the MeOH was evaporated under vacuum to recover 2.883 g of the hydrochloride salt.

'H-NMR (CDCl$_3$): δ=2.86 (brd.), 3.37(s,3H), 3.92(s,3H), 7.13(d, 2H) and 7.94(d,2H) ppm.

IR(CDCl$_3$): V max=1801, 1751, 1718 cm$^{-1}$.

Analysis Calcd. for $C_{46}H_{72}ClNO_{16}$(930.526):
C, 59.38; H, 7.80; N, 1.51; Cl, 3.81.
Found: C, 59.23; H, 7.75; N, 1.49; Cl, 3.67.

EXAMPLE 31

4"-glycylerythromycin A 11,12-carbonate
6,9-hemiacetal

2'-Acetylerythromycin A 11,12-carbonate-6,9hemiacetal (2.503 g; 3.12 mmol), DMAP (0.781 g; 6.39 mmol), diisopropyl ethylamine (0.55 ml; 3.17 mmol) and N-CBZ glycine (1.967 g; 9.40 mmol) were all measured out and added to a 250 mL flask equipped with magnetic stir bar and drying tube. 125 mL of CH$_2$Cl$_2$ was added to dissolve all reagents. The solution was cooled to 0° C. in an ice bath. 2.000 g (9.69 mmol) of DCC was measured out and added to the cold solution. The reaction was stirred for 30 mins, then allowed to stand at 0° C. for 18 hrs. After 18 hrs, the contents of the flask were filtered to remove the bulk of the DCU which had formed. The filtered CH$_2$Cl$_2$ solution was then evaporated in vacuo and the residue was taken up in CH$_3$CN. The CH$_3$CN solution was allowed to stand for 30 minutes at room temperature then refiltered. The refiltered solution was then evaporated under vacuum to yield 4.570 g of crude glassy solid. Glass was flash chromatographed on a silica gel column to yield 1.607 g of pure 2'-acetyl-4"-(N-CBZ-glycyl)erythromycin A 11,12-carbonate-6,9-hemiacetal.

1.60 g of 2'-Acetyl-4"-N-CBZ-glycylerythromycin A 11,12-Carbonate-6,9-hemiacetal was dissolved in 100 mL of absolute MeOH and allowed to stand at room temperature for 4 days. The solvent was evaporated in vacuo to yield 1.531 g of the corresponding deacetylated product.

1.53 g of 4"-(N-CBZ-glycyl)erythromycin A 11,12-carbonate-6,9-hemiacetal was hydrogenated in methanol over 20% Pd-C to remove the N-CBZ group.

After 1.5 hours the solution was filtered by gravity under argon and then refiltered using a Millipore EH membrane filter. The resulting solution was evaporated in vacuo to a colorless glassy solid. The glass was dried at room temperature for 18 hrs in a vacuum oven to give 1.218 g of product.

EXAMPLE 32

4"-(2-Naphthoyl Glycyl) Erythromycin A
11,12-carbonate-6,9-Hemiacetal 0.504 g (0.0617 mmol) of 4"-glycylerythromycin A 11,12-carbonate-6,9-hemiacetal and 0.265 g (1.28 mmol) of DCC were added to a 100 mL flask equipped with a stir bar and CaSO$_4$ drying tube. The above reagents were then dissolved in 20 mL of THF which had been dried over 3A molecular sieves. The solution was then cooled to 0° C. using an ice bath. After cooling, 0.212 g (1.23 mmol) of 2-naphthoic acid was added and the solution was stirred at 0° C. After 4 hrs., an additional 0.213 g (1.24 mmol) of 2-naphthoic acid and 0.265 g (1.28 mmol) of DCC were added to the solution which was stirred for another 1.5 hrs. The reaction was then allowed to stand at 0° C. for 22 hrs.

The solution was filtered and evaporated to dryness. The residue was taken up in CH$_3$CN and allowed to stand until crystals, found to be 2-naphthol anhydride, formed. The anhydride crystals were filtered and discarded. The liquor was evaporated to dryness and the residue was taken up in 100 mls of ethyl acetate. This solution was washed with 4×50 mL of 4% aqueous NaHCO$_3$ solution followed by 100 mL of saturated aqueous NaCl solution. The ethyl acetate portion was evaporated to dryness under vacuum to give 0.704 g of a glassy solid.

The crude solid was column chromatographed on a silica gel column to yield 272 mg of pure 4"-(2-naphthoyl)glycylerythromycin A 11,12-carbonate 6,9-hemiacetal as a light yellow glassy solid.

'H-NMR (CDCl$_3$): δ=2.31(s,6H), 3.35(s,3H), 6.86(t,1H), 7.58(m, 2H), 7.91 (m, 4H) and 8.35 (brd. s, 1H) ppm.

IR (CCl$_4$): V max=1818, 1753, 1678 cm$^{-1}$.

Analysis Calcd. for C$_{51}$H$_{74}$N$_2$O$_{16}$(971.162):
C, 63.08, H, 7.68; N, 2.88.

Found: C, 62.48; H, 7.63; N, 2.88.

EXAMPLE 33

4"-(2-Furoyl)erythromycin
11,12-carbonate-6,9-hemiacetal

A mixture of 4.00 g (4.99 mmol) of 2'-acetylerythromycin A 11,12 carbonate-6,9-hemiacetal and 1.67 g (13.70 mmol) of 4-dimethylaminopyridine was dissolved in 100 mL of CH$_2$Cl$_2$ and was cooled to 0°–5° C. in an ice-bath. Then 1.63 g (12.48 mmol) of 2-furoyl chloride were added with stirring and the reaction was kept at 0° C. for 18 hours. Excess 2-furoyl chloride was consumed by reaction with N-methylpiperazine (8.3 g, 7,49 mmol) for 2 hours at 0° C. The CH$_2$Cl$_2$ was evaporated and the residue was dissolved in 200 mL of ethyl acetate. The ethyl acetate solution was washed with two 100 mL portions of pH 6.0 phosphate buffer followed by two 100 mL portions of 4% aqueous NaHCO$_3$. The ethyl acetate was dried over anhydrous Na$_2$SO$_4$ and was evaporated in vacuo to yield 4.16 g of 2'-acetyl-4"-(2-furoyl)erythromycin A 11,12-carbonate-6,9-hemiketal as a glass.

The acetyl derivative was dissolved in 100 mL of methanol and the solution was kept at 25° C. for 3 days. The light yellow solution was treated with 1.6 g of charcoal, was filtered and was evaporated to yield 4"-(2-furoyl)erythromycin A 11,12-carbonate 6,9-hemiacetal which was crystallized from acetonitrile to yield 2.58 g of white crystals, mp. 160°–167° C.

Analysis Calcd. for C$_{43}$H$_{67}$NO$_{16}$·H$_2$O. 0.5 CH$_3$CN(892.552):
C, 59.21; H, 7.96; N, 2.35.

Found: C, 59.60; H, 7.73; N, 2.54.

'H-NMR (CDCl$_3$): δ=0.95 (t, 3H), 1.35 (S, 3H), 2.32 (S, 6H), 3.35 (S, 3H), nd 4.60 (d, 1H), 6.52 (dd, 1H), 7.20 (d, 1H) and 7.58 (brd. S, 1H) ppm IR (CDCl$_3$): V$_{max}$=3530, 3460, 1800, and 1730 cm$^{-1}$.

EXAMPLE 34

4"-(2-Furoyl)erythromycin A
11,12-carbonate-6,9-hemiacetal hydrochloride salt

A mixture of 2.01 g of 4"-(2-furoyl) erythromycin A 11,12-carbonate-6,9-hemiketal and 0.12 g of ammonium chloride was dissolved in 50 mL of methanol. The methanol was evaporated in vacuo to yield 2.02 g of the hydrochloride salt as a glass.

Analysis Calcd. for C$_{43}$H$_{68}$ClNO$_{16}$(890.472):
C, 58.00; H, 7.70; N, 1.57; Cl, 3.98.

Found: C, 57.42; H, 7.79; N, 1.45; Cl, 4.23.

'H-NMR(CDCl$_3$): δ=0.95 (t, 3H), 1.30 (S, 3H), 2.8 (broad, 6H), 3.35 (S, 3H), and 4.58 (d, 1H) ppm.

IR (CDCl$_3$): V$_{max}$=3530, 1805, and 1730 cm$^{-1}$.

Dosage and Administration

This invention also provides pharmaceutical compositions in unit dosage form, comprising a compound of the foregoing type in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such peanut oil, cotton seed oil, sesame oil, olive oil, corn oil and soybean oil; polyols such as propylene glycol, glycerin, sorbitol, mannitol and polyethylene glycol; injectable esters such as ethyl oleate and ethyl laurate; agar; buffering agents such as magnesium hydroxide and aluminum hydroxide; alginic acid; pyrogen-free water; isotonic saline; ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

This invention also provides methods of treating and preventing infection by susceptible organisms in a human or lower animal host in need of such treatment, which method comprises administration to the human or lower animal host a therapeutically effective amount of a compound of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intraarticular and intrathecal injection and infusion techniques.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the erythronolide antibiotic herein is meant a sufficient amount of the antibiotic compound to treat or prevent susceptible bacterial or other microbial infections, at a reasonable benefit/risk ratio applicable to any medical treatment. Total daily dose of the compounds of this invention administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose. Generally, when the therapeutic agent moiety is 4''-acetylerythromycin A 11,12-carbonate-6,9-hemiacetal, dosage levels of about 0.1 mg to about 1000 mg, more preferably about 0.25 mg to about 750 mg and most preferably about 0.5 mg to about 500 mg. of active ingredient per kg. of body weight are administered daily to a mammalian patient suffering from an infection caused by a susceptible organism. If desired, the daily dose may be divided into multiple doses for administration, e.g., two to four times per day. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

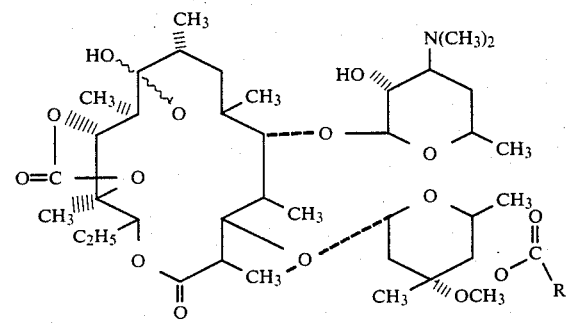

wherein R is lower alkyl, aryl, alkene, aryl halide, alkylamino and furanyl or pharmaceutically acceptable salts thereof.

2. A pharmaceutical composition comprising a therapeutically effective amount of a compound of claim 1 and a pharmaceutically acceptable carrier.

3. A method of treating and preventing bacterial infections in humans and lower animals in need of such treatment, comprising administering to the human or lower animal a therapeutically effective amount of a compound according to claim 1.

* * * * *